(12) United States Patent
Bowie

(10) Patent No.: US 8,122,774 B2
(45) Date of Patent: Feb. 28, 2012

(54) TEST TOOL

(75) Inventor: Angus George Bowie, Scotland (GB)

(73) Assignee: Stats (UK) Limited, Aberdeen (GB)

(*) Notice: Subject to any disclaimer, the term of this patent is extended or adjusted under 35 U.S.C. 154(b) by 9 days.

(21) Appl. No.: 12/401,941

(22) Filed: Mar. 11, 2009

(65) Prior Publication Data

US 2009/0229373 A1 Sep. 17, 2009

(30) Foreign Application Priority Data

Mar. 12, 2008 (GB) .................................. 0804582.5

(51) Int. Cl.
*G01N 3/08* (2006.01)
(52) U.S. Cl. ........................................................ 73/837
(58) Field of Classification Search .................... 73/837, 73/760, 856–860
See application file for complete search history.

(56) References Cited

U.S. PATENT DOCUMENTS

| | | | |
|---|---|---|---|
| 3,823,605 A * | 7/1974 | Schmitz et al. .................. 73/774 |
| 3,954,005 A * | 5/1976 | Edwards ........................ 73/833 |
| 4,458,522 A * | 7/1984 | Toelke ............................ 73/49.5 |
| 5,419,184 A | 5/1995 | Pace | |
| 5,797,431 A | 8/1998 | Adams | |
| 6,463,791 B1 | 10/2002 | Berube et al. | |
| 6,976,536 B2 * | 12/2005 | Simpson et al. ............. 166/277 |
| 7,669,482 B2 * | 3/2010 | Jacobs et al. .................... 73/841 |
| 7,739,917 B2 * | 6/2010 | Shuster et al. ................... 73/789 |
| 7,874,217 B2 | 1/2011 | Carson | |
| 2004/0065445 A1 * | 4/2004 | Simpson et al. ............. 166/382 |
| 2009/0229349 A1 * | 9/2009 | Bowie ............................ 73/49.5 |

FOREIGN PATENT DOCUMENTS

| | | |
|---|---|---|
| JP | 56-18741 | 2/1981 |
| JP | 59-26033 | 2/1984 |
| JP | 2002-323419 | 11/2002 |
| RU | 2150686 | 6/2000 |

OTHER PUBLICATIONS

United Kingdom Combined Search and Examination Report dated Jul. 14, 2008.

* cited by examiner

*Primary Examiner* — Max Noori
(74) *Attorney, Agent, or Firm* — Carlson, Gaskey & Olds, P.C.

(57) ABSTRACT

A test tool assembly for use in testing a tubular component, such as a pipe section, is mounted on the exterior surface of the pipe section. The assembly includes a force-generating arrangement for generating and applying an axial load to the pipe section. One end of the force-generating arrangement is secured to an outer surface of the pipe section by a split sleeve clamp mounted on an external gripping member. The other end of the arrangement features sockets which engage nuts provided on studs which extend into bolt holes in the pipe section. The force-generating arrangement further includes an array of hydraulic actuators mounted around the pipe section between the split sleeve clamp and the sockets. The tool assembly will typically be used in combination with a pressure test tool.

22 Claims, 1 Drawing Sheet

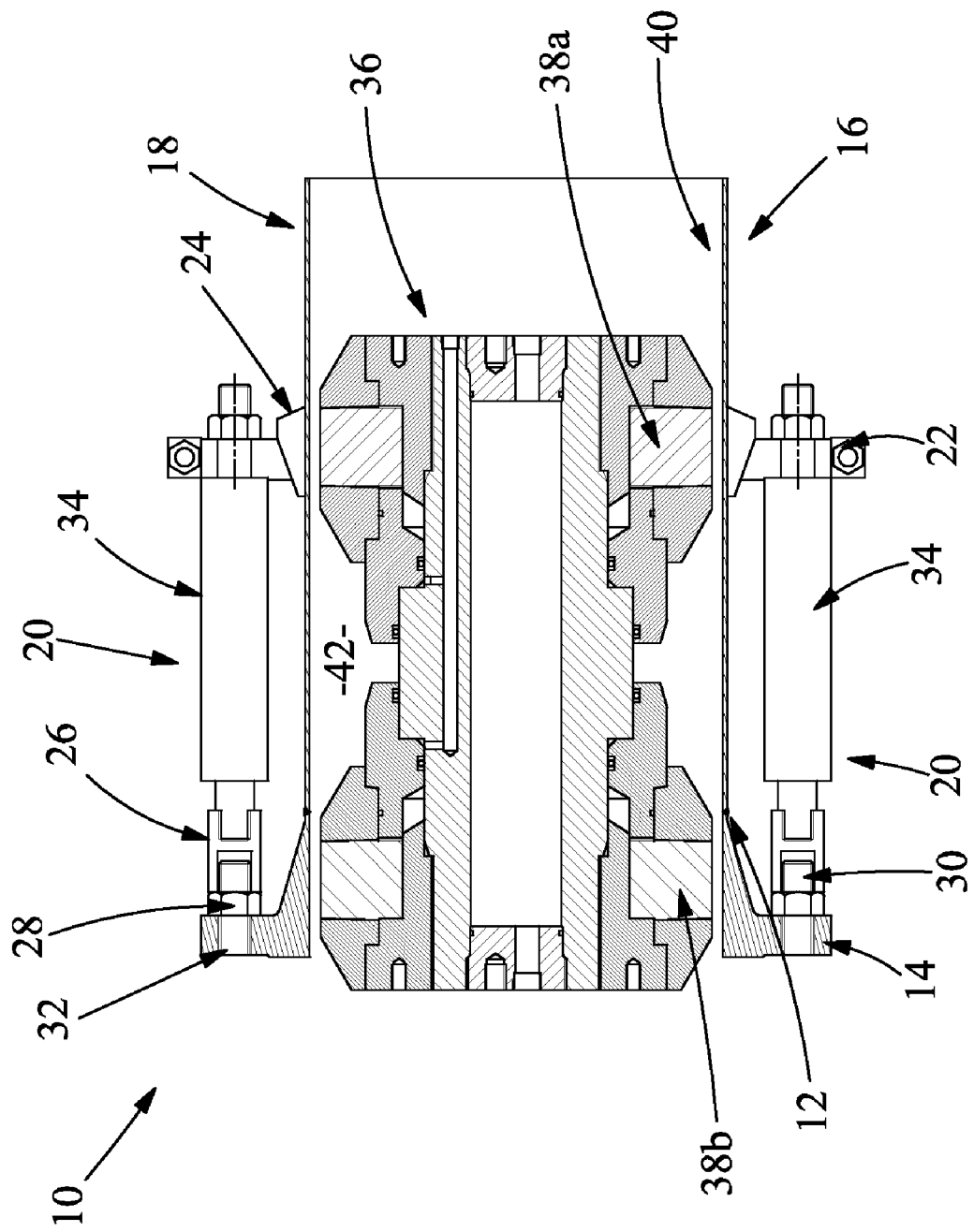

TEST TOOL

REFERENCE TO RELATED APPLICATION

This application claims priority to United Kingdom Patent Application No. 0804582.5 filed Mar. 12, 2008.

FIELD OF THE INVENTION

This invention relates to a test tool and in particular, but not exclusively, to a test tool for testing the strength of a tubular component.

BACKGROUND OF THE INVENTION

Many industries make use of tubular components such as pipes, tubes, pipe modules, pipelines or the like to transport fluid over distance. For example, in the oil and gas industry, a pipeline may comprise a series of pipe modules which are transported to and assembled on site via bolted or welded flange connections. Each module may also comprise a number of components coupled together. For example, a typical flange connection on a pipe section comprises a radially extending flange which is welded to an end of the pipe section, the flange being suitable for bolting or welding to a similar flange on another section of pipe.

A number of tools have been developed which permit the integrity of a section of pipe, in particular, but not exclusively, the welds of the pipe, to be tested for leakage.

In the case of a flange connection, tools have been developed which permit the flange weld to be pressure tested. For example, one tool comprises a flanged end which, on insertion of the tool into the pipe, is coupled to the flanged end of the pipe to be tested. The tool flange and pipe flange are typically bolted together to form a flange connection, though other means for securing the flange connection can be used. The tool further comprises a seal unit spaced from the flange connection, the flange and seal unit defining an annular volume. In use, the tool is inserted into the pipe such that the flange connection and seal unit straddle the section of the pipe and/or the weld to be tested. Pressurized fluid is inserted through a port in the tool flange into the annular volume, thereby applying a test pressure between the flange connection and the seal unit. The pressure of the fluid in the annular volume is monitored so that the integrity of the weld can be assessed.

An alternative tool is used for pressure testing an annular section of a pipe and comprises two axially spaced seals located on a body. On insertion into the pipe to be tested, the seals are energized such that the seals, the body and the pipe wall define an annular volume into which pressurized fluid may be inserted to apply a test pressure between the seals. The pressure of the fluid in the annular volume is monitored so that the integrity of the weld can be assessed, a drop in pressure indicating that the weld may have failed.

In each case, the tool applies a radial load to the pipe section being tested, the load being the test pressure multiplied by the area of pipe wall exposed to the test pressure. The tools are typically designed to minimize generation of axial loading by minimizing the depth of the annular volume and the test pressure generated axial loads tend to be restrained by or transferred through the tool body.

Thus, while the pressure test provided by conventional tools establishes the pressure integrity of the pipe section, they do not provide a complete assessment of the strength capability of the pipe section and/or weld to be tested.

SUMMARY OF THE INVENTION

According to a first aspect of the present invention there is provided a method of testing a tubular component, the method comprising the steps of engaging first and second portions of a wall of a tubular component with first and second engaging elements, and applying an axial tensile test load to the wall of the component via the engaging elements.

According to a second aspect of the present invention, there is provided a method of testing a tubular component, the method comprising the steps of applying a fluid pressure to a section of a wall of a tubular component, and applying an axial load to said wall section.

The method may further comprise monitoring the axial load and/or applying a predetermined or selected axial load to test the strength of the tubular component.

By monitoring the fluid pressure while applying the axial load, the strength and integrity of the tubular component may be tested, the test loading the component in a similar manner to that experienced by a tubular component in use, when forming part of a pipe assembly and filled with pressurized fluid.

According to a further aspect of the present invention, there is provided a test tool assembly for use in testing a tubular component, the tool assembly comprising first and second elements adapted to engage portions of a tubular component, and a force-generating arrangement adapted to apply an axial load to the tubular component via the elements.

Where traditionally pressure test tools have sought to minimize generation of axial loads, a test method and test tool assembly according to embodiments of the present invention is intended to or adapted to apply an axial load to a tubular component to facilitate localized strength testing of the tubular component. For example, but not exclusively, a method and a tool assembly according to embodiments of the present invention may be used to test the strength of a tubular component, a portion of a tubular component and/or a connection such as a weld or the like.

The force-generating arrangement may comprise a hydraulic arrangement such as a hydraulic piston arrangement or the like. Alternatively, or in addition, the force-generating arrangement may comprise a pneumatic arrangement and/or a mechanical arrangement such as a screw or the like. In the case of a mechanical arrangement, torque may be applied via the screw to generate the required axial force on the engaging elements.

The test tool assembly may comprise at least one gripping element adapted to engage the tubular component. The, or each, gripping element may be adapted to secure the force-generating arrangement to the tubular component and, in use, the force-generating arrangement may be adapted to apply the axial test load to the tubular component via the gripping element.

In particular embodiments, one gripping element is adapted to engage the tubular component. Alternatively, two or more gripping element may be provided to engage the tubular component. For example, the tool assembly may comprise two axially spaced gripping elements adapted to engage the tubular component.

The, or each, gripping element may comprise a single gripping member or alternatively the gripping element may comprise a plurality of gripping members. For example, in one embodiment the, or each, gripping element comprises a taper lock. Alternatively, or in addition, the gripping element may comprise a clamp, a bearing member such as ball bearings or any other suitable gripping element.

The assembly may comprise an element for engaging a part or component of a tubular component, such as a flange. In one embodiment, the assembly includes an arrangement for engaging a flange via studs or bolts mounted to a flange.

The force-generating arrangement may be adapted to apply a tensile test force or load to the tubular component to test the tensile strength of the tubular component.

The tool assembly may, for example, be adapted to apply a test force up to a selected test threshold.

At least one of the first and second engaging elements may be adapted to engage an exterior portion of the tubular component. Alternatively, at least one of the first and second engaging elements may be adapted to engage an interior portion of the tubular component.

The assembly may be used in combination with a pressure test tool, which applies a fluid pressure to the wall of the tubular component.

In particular embodiments, the pressure test tool may comprise seal elements adapted to engage the tubular component and the gripping elements and/or flange engaging element may be located adjacent to the seal elements.

BRIEF DESCRIPTION OF THE DRAWING

These and other aspects of the present invention will now be described, by way of example only, with reference to the accompanying FIG. 1, a diagrammatic cross-sectional view of a tool assembly according to an embodiment of the present invention.

DETAILED DESCRIPTION OF THE DRAWING

FIG. 1 shows a test tool assembly 10 according to an embodiment of the present invention. The assembly 10 is being utilized to test the strength of a welded joint 12 mounting a flange 14 to the end of a pipe section 16.

The tool assembly 10 is mounted on the exterior surface 18 of the pipe section 16 and comprises a force-generating arrangement 20 for generating and applying an axial load to the pipe section 16 and flange 14. One end of the force-generating arrangement 20 is secured to the pipe section outer surface 18 by a split sleeve clamp 22 mounted on an external gripping member 24. In the embodiment shown in the Figure, the gripping member 24 comprises a taper lock, though it will be understood that any suitable mechanism for gripping the pipe section outer surface 18, such as ball grippers, may be used where appropriate. The other end of the arrangement 20 features sockets 26 which engage nuts 28 provided on studs 30 which extend into bolt holes 32 in the flange 14.

External location of the force-generating arrangement 20 is most applicable to smaller diameter pipe sections 16 where there is insufficient space to package the tool assembly 10 internally of the pipe section 16 or where it is desired to have easy access to the force-generating arrangement 20.

The force-generating arrangement 20 further comprises an array of hydraulic actuators 34 (two actuators are shown) mounted around the pipe section 16 between the split sleeve clamp 22 and the flange sockets 26.

The tool assembly 10 will typically be used in combination with a pressure test tool, and the Figure illustrates such a tool 36 located within the pipe section 16. The tool 36, shown in an inactive configuration, includes seals 38a, 38b which may be energized to engage a wall 40 of the pipe section 16. Pressurized fluid may then be supplied to an annulus 42 between the seals 38a, 38b and the wall 40. The applied test pressure is monitored to determine the integrity of the joint 12. It will be noted that the external gripping member 24 and the internal seal 38a are opposing, minimizing unbalanced loading on the pipe wall 40. The other seal 38b is located within the heavier section flange 14.

Simultaneously with the application of the test pressure to the annulus 42, hydraulic fluid is supplied to the actuators 34 to provide a predetermined axial test load across a test boundary of the pipe section 16 via the gripping member 24 and flange sockets 26.

Those of skill in the art will further recognise that the illustrated tool assembly is merely exemplary of the present invention and that the same objectives may be achieved by using a variety of different configurations. For example, the tool assembly may be used in conjunction with a flange leak test tool.

Furthermore, though tool activation has been described in relation to pressurized fluid activation, the axial load could be produced by mechanical means such as by applying a torque force to the tool to apply an axial load to the engaging elements. For example, the axial load could be applied mechanically for example using a bolt array. Ideally the lock segments will be located adjacent to the leak test tool seal to minimize pipe stresses.

The assembly may comprise two axially spaced gripping elements, such as taper locks, for engaging the pipe section. The force-generating arrangement may be provided between the gripping elements.

Accordingly, it will be understood that tool assemblies according to embodiments of the present invention may be used in combination with any known pipe test tool to provide the additional functionality of performing axial strength testing.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed:

1. A method of testing a tubular component, the method comprising:
   mounting a test tool assembly on a tubular component to be tested;
   engaging first and second portions of a wall of a tubular component with first and second engaging elements of the test tool assembly, wherein at least one of the first and second engaging elements comprise a gripping element adapted to engage an external wall of the tubular component;
   applying a fluid pressure to a section of the wall of the tubular component using a pressure test tool having a seal element adapted to engage an internal wall of the tubular component to be tested; and
   applying an axial test load to the wall of the tubular component via the first and second engaging elements, wherein radial forces exerted on the tubular component by the gripping element of the test tool assembly and the seal element of the pressure test tool are opposed.

2. The method of claim 1, comprising the step of monitoring the axial test load.

3. The method of claim 1, comprising applying a predetermined or selected axial load.

4. The method of claim 1, comprising the step of monitoring the fluid pressure while applying the axial test load.

5. A test tool assembly for use in testing a tubular component and adapted to be mounted on the tubular component to be tested, the test tool assembly comprising:
first and second engaging elements adapted to engage first and second portions of a wall of a tubular component to be tested, wherein at least one of the first and second engaging elements comprises a gripping element adapted to engage an external wall of the tubular component to be tested; and
a force-generating arrangement adapted to apply an axial test load to the tubular component via the first and second engaging elements while a fluid pressure is applied to a section of the wall of the tubular component to be tested by a pressure test tool having a seal element adapted to engage an internal wall of the tubular component to be tested, wherein the test tool assembly is configured so that radial forces exerted on the tubular component by the gripping element of the test tool assembly and the seal element of the pressure test tool are opposed.

6. The tool assembly of claim 5, wherein the force-generating arrangement comprises at least one of a hydraulic arrangement, a pneumatic arrangement, and a mechanical arrangement.

7. The tool assembly of claim 5, wherein the gripping element is adapted to secure the force-generating arrangement to the tubular component.

8. The tool assembly of claim 5, wherein the force-generating generating arrangement is adapted to apply the axial test load to the tubular component via the gripping element.

9. The tool assembly of claim 5, wherein the gripping element comprises a single gripping member.

10. The tool assembly of claim 5, wherein the gripping element comprises a plurality of gripping members.

11. The tool assembly of claim 5, wherein the at least one gripping element comprises a taper lock.

12. The tool assembly of claim 5, comprises an element for engaging a flange of the tubular component.

13. The tool assembly of claim 12, wherein the element is adapted to engage the flange via studs.

14. The tool assembly of claim 5, wherein the force-generating arrangement is adapted to apply a tensile test force to the tubular component.

15. The tool assembly of claim 5, wherein the force-generating arrangement is adapted to apply a test force up to a selected threshold.

16. The tool assembly of claim 5, wherein one of the first and second engaging elements is adapted to engage the internal wall of the tubular component.

17. The tool assembly of claim 5 in combination with a pressure test tool.

18. The tool assembly of claim 17, wherein the pressure test tool is adapted for location within the tubular component to be tested.

19. The method of claim 1, wherein the step of applying the fluid pressure to the section of the wall of the tubular component comprises applying the fluid pressure to the internal wall of the tubular component.

20. The method of claim 1, wherein the step of applying the axial test load comprises applying an axial tensile test load to the wall of the tubular component.

21. The method of claim 1, wherein the gripping element of the test tool assembly and the seal element of the pressure test tool are axially aligned.

22. The tool assembly of claim 5, wherein the gripping element of the test tool assembly and the seal element of the pressure test tool are axially aligned.

* * * * *